US00PP08571P

United States Patent [19]

van Andel

[11] Patent Number: Plant 8,571

[45] Date of Patent: Feb. 1, 1994

[54] STANDARD CARNATION NAMED STATAS

[75] Inventor: Jacob van Andel, Aalsmeer, Netherlands

[73] Assignee: Van Staaveren B.V., Aalsmeer, Netherlands

[21] Appl. No.: 782,082

[22] Filed: Oct. 24, 1991

[51] Int. Cl.[5] ..... A01H 5/00

[52] U.S. Cl. ..... Plt./71.1

[58] Field of Search ..... Plt. 71.1, 72.1

*Primary Examiner*—Howard J. Locker

*Attorney, Agent, or Firm*—Tilton, Fallon, Lungmus & Chestnut

[57] ABSTRACT

A new and original carnation cultivar particularly distinguished by profuse and recurrent production of empire rose blossoms, which are borne singularly on strong upright stems on a plant which has a strong and vigorous growth habit and a height of greater than 90 centimeters.

1 Drawing Sheet

BACKGROUND OF THE NEW PLANT

This new carnation cultivar originated as a hybrid seedling developed by me in 1985 at our nursery in Aalsmeer, Holland by crossing two varieties selected from our collection of carnations maintained for breeding purposes at Aalsmeer. The seed parent is Barlo. Barlo has more splitting calyxes than Statas and a weaker stem. The leaves are broader and longer and more curled. The pollen parent is Klekopi. The growth rate of Statas is much faster than the growth rate of Klekopi. The color of Klekopi is paler pink than Statas. This particular seedling was selected for propagation because of its empire rose flowers, and the overall high quality of its growth havit. Asexual propagation of this selected plant was done by means of cuttings, under my direction at Aalsmeer. Propagation of this new plant continued from generation to generation to determine whether the novel characteristics of this selected seedling would hold true from generation to generation so that its homogeneity could be assured. This proved to be successful and this new carnation variety is now being propagated at Aalsmeer.

DESCRIPTION OF THE DRAWING

My new carnation cultivar is illustrated by the accompanying photographic drawing, which shows blooming portions of flower stems with the flower shown in full development, the color rendition being as nearly true to that herein specified as is reasonably possible to obtain by professional photographic procedures.

DESCRIPTION OF THE NEW PLANT

The following is a detailed description of my new carnation variety based upon observation of plants grown in greenhouse as well as outdoors at Aalsmeer and blooming during the current year. The color designations stated herein are according to the R.H.S. Colour Chart published by the Royal Horticultural Society of London, England.

THE PLANT

Origin: Seedling

Parentage:

*Seed parent.*—Barlo (unpatented).

*Pollen parent.*—Klekopi U.S. Plant Pat. No. 6,444.

Classification: *Dianthus caryophyllus.*

*Botanic.*—Commercial standard carnation.

Form: Tall, vigorous bush.

Height: Greater than 90 cm, in average.

Main stem: 90 cm. or greater in average.

*Growth.*—Fast, vigorous and strong.

Branching character: No branching.

Foliage:

*Number of leaves.*—26-30.

*Leaf size.*—Twelve by 0.7 centimeters at the fifth node.

*Shape.*—Lanceolate.

*Margins.*—Entire and straight.

*Texture.*—Leathery.

*Color.*—Upper side: R.H.S. 122-C Reverse side: 122-C.

THE BUD

Color: Both upper and underside are dark gray/green.

The bud size:

*Medium diameter.*—averaging about 2 cm.

*Length.*—averaging about 3.5 cm.

*Shape.*—Ovoid.

Calyx:

*Shape.*—Cylindrical.

*Size.*—Averaging about 2 cm. in width and 3.5 cm. in length.

*Splitting.*—The calyx does not split.

*Aspect.*—Smooth color; R.H.S. 143C.

THE FLOWER

Blooming habit: Recurrent and profuse.

Size of flower: Medium.

*Diameter.*—Averaging about 6 cm.

*Depth.*—Averaging about 2 cm.

Borne: Singly.

Shape:

*When first opening.*—Flat.

*When mature.*—High center.

Petalage:

*Number of petals.*—65-75.

*Texture.*—Soft.

*Appearance.*—Velvety.

Color: Both outer and inside petals:

*Body.*—48-D.

*Base.*—155-D.

*Reverse side.*—48-D.

Flower stem:

*Length.*—Averaging greater than 90 cm.

*Color.*—R.H.S. 122C.

*Character.*—Strong and upright; erect.

Persistence: The flowers hang on and dry.

Lasting quality:

As a cut flower.—About fifteen (15) days in a vase.

*On the plant.*—About twenty-one (21) days.

Fragrance: absent.

Disease resistance: Moderately resistant to Fusarium.

REPRODUCTIVE ORGANS

Stamens:

*Number.*—About ten, in average.

*Arrangement.*—Petaloid/rudimental.

Anthers:

*Size.*—3 mm.

*Color.*—White.

Filaments: Averaging between 3 and 4 cm.

*Color.*—White.

Pollen: Absent.

Pistils:

*Number.*—One.

*Styles.*—About 2.5-3 cm., in average length.

*Color.*—White.

Stigmas:

*Color.*—White.

FRUIT

Fertility: The fruit is not fertile.

I claim:

1. A new and distinctive carnation cultivar, substantially as herein shown and described, particularly characterized by its medium sized, empire rose flowers, which bloom profusely and recurrently and are borne singly on the strong, upright stems of this tall, vigorous bush.

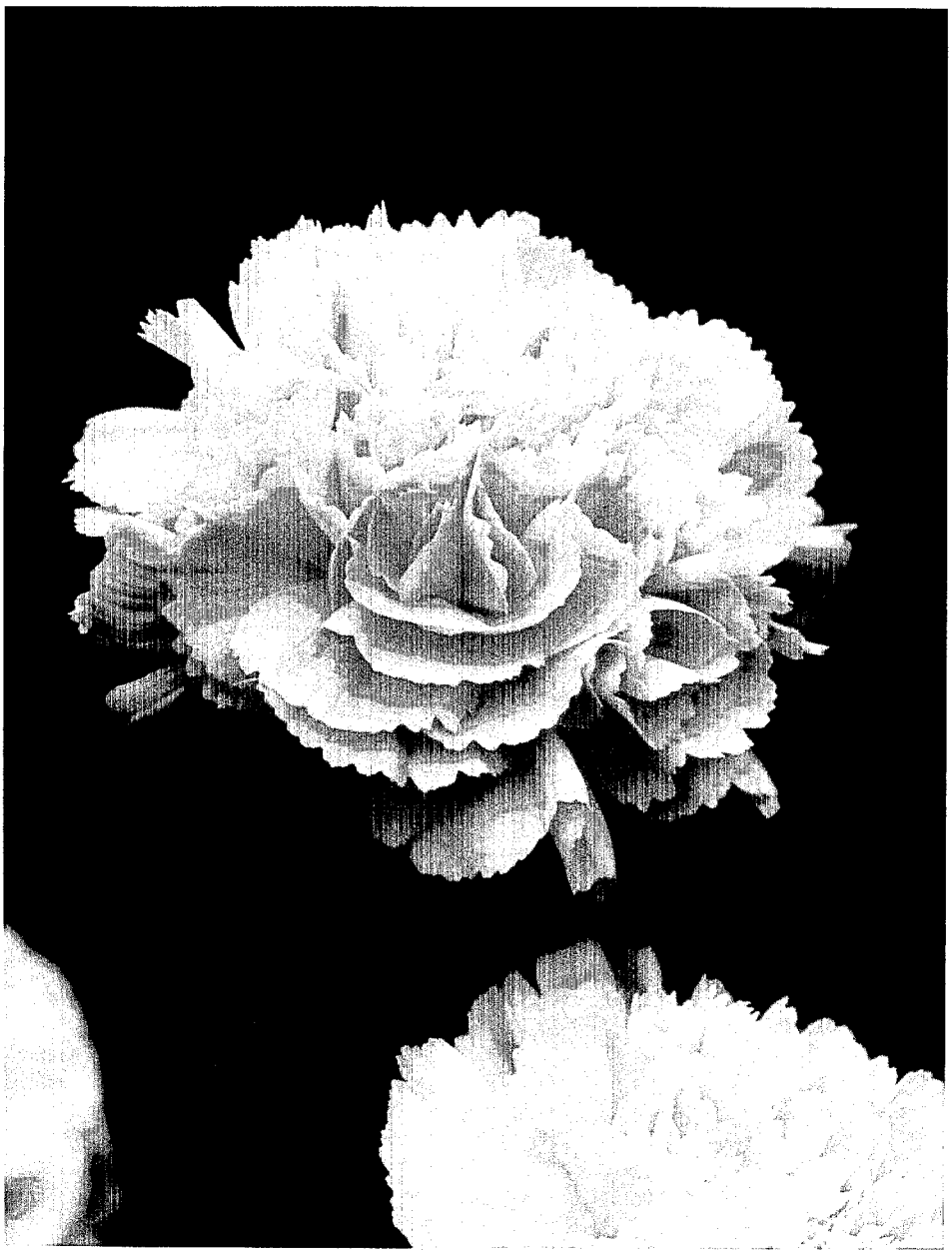

* * * * *